US011471562B2

(12) United States Patent
Lin et al.

(10) Patent No.: US 11,471,562 B2
(45) Date of Patent: Oct. 18, 2022

(54) CARTILAGE MATERIAL HAVING MINIMAL HYPERTROPHY AND ROBUST INTEGRATION CAPACITY, AND USES THEREFOR

(71) Applicant: University of Pittsburgh—Of the Commonwealth System of Higher Education, Pittsburgh, PA (US)

(72) Inventors: Hang Lin, Pittsburgh, PA (US); Rocky Sung Chi Tuan, Pittsburgh, PA (US); Yuanheng Yang, Changsha (CN)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 627 days.

(21) Appl. No.: 16/379,147

(22) Filed: Apr. 9, 2019

(65) Prior Publication Data

US 2019/0307922 A1   Oct. 10, 2019

Related U.S. Application Data

(60) Provisional application No. 62/654,800, filed on Apr. 9, 2018.

(51) Int. Cl.
| | | |
|---|---|---|
| *A61L 27/36* | (2006.01) | |
| *A61K 35/28* | (2015.01) | |
| *C12N 5/077* | (2010.01) | |

(52) U.S. Cl.
CPC .......... *A61L 27/3687* (2013.01); *A61K 35/28* (2013.01); *A61L 27/3654* (2013.01); *C12N 5/0655* (2013.01); *A61L 2430/06* (2013.01); *A61L 2430/40* (2013.01); *C12N 2501/119* (2013.01); *C12N 2501/15* (2013.01); *C12N 2501/155* (2013.01); *C12N 2501/19* (2013.01); *C12N 2506/1353* (2013.01); *C12N 2506/1384* (2013.01); *C12N 2509/00* (2013.01)

(58) Field of Classification Search
None
See application file for complete search history.

(56) References Cited

U.S. PATENT DOCUMENTS

| | | |
|---|---|---|
| 6,429,013 B1 | 8/2002 | Halvorsen et al. |
| 10,066,209 B2 | 9/2018 | Phan |
| 2010/0003299 A1* | 1/2010 | Tseng .................... A61K 35/44 424/423 |

OTHER PUBLICATIONS

Lee et al., International Journal of Molecular Sciences 2017, 18, 1320, 14 pages (Year: 2017).*
Yorukoglu et al., Stem Cells International, vol. 2017, Article ID 2374161, 13 pages (Year: 2017).*
Motoike et al., Cryopreserved clumps of mesenchymal stem cell/extracellular matrix complexes retain osteogenic capacity and induce bone regeneration, Stem Cell Research & Therapy (2018) 9:73, 13 pages, published online Mar. 21, 2018 (Year: 2018).*
Bhumiratana et al., "Large, stratified, and mechanically functional human cartilage grown in vitro by mesenchymal condensation", PNAS, May 13, 2014, pp. 6940-6945, vol. 111, No. 19.
Dang et al., "Driving Cartilage Formation in High-Density Human Adipose-Derived Stem Cell Aggregate and Sheet Constructs Without Exogenous Growth Factor Delivery", Tissue Engineering: Part A, 2014, pp. 3163-3175, vol. 20, Nos. 23 and 24.
Diedrichs et al., "Functional Comparison of Human-Induced Pluripotent Stem Cell-Derived Mesenchymal Cells and Bone Marrow-Derived Mesenchymal Stromal Cells from the Same Donor", Stem Cells and Development, 2014, pp. 1594-1610, vol. 23, No. 14.
Lin et al., "Cartilage Tissue Engineering Application of Injectable Gelatin Hydrogel with In Situ Visible-Light-Activated Gelation Capability in Both Air and Aqueous Solution", Tissue Engineering: Part A, 2014, pp. 2402-2411, vol. 20, Nos. 17 and 18.
Long et al., "The effect of mesenchymal stem cell sheets on structural allograft healing of critical-sized femoral defects in mice", Biomaterials, 2014, pp. 2752-2759, vol. 35, No. 9.
Raposio et al., "Adipose-derived stem cells: Comparison between two methods of isolation for clinical applications", Annals of Medicine and Surgery, 2017, pp. 87-91, vol. 20.
Richardson et al., "Mesenchymal stem cells in regenerative medicine: Focus on articular cartilage and invertebral disc regeneration", 2016, Methods, pp. 69-80, vol. 99.
Singh et al., "Induced pluripotent stem cells: applications in regenerative medicine, disease modeling, and drug discovery", Frontiers in Cell and Developmental Biology, 2015, 18 pages, vol. 3, Article 2.
Yang et al., TERMIS-AM 2017 Annual Conference, Dec. 3, 2017, 1 page, Charlotte, NC.

* cited by examiner

*Primary Examiner* — Evelyn Y Pyla
(74) *Attorney, Agent, or Firm* — The Webb Law Firm

(57) ABSTRACT

A method is provided for producing a live cartilaginous material useful for implantation into a patient. A method of treating a patient comprising implanting a cartilaginous material prepared according to the provided method in an anatomical site in a patient also is provided.

20 Claims, 13 Drawing Sheets

Mean thicknesses of naturally occurring cartilage
Knees: 1.69-2.0 mm

Compressive modulus of naturally occurring cartilage:
~.8-1.5 MPa

| Condition | Thickness (μm) | E (kPa) |
|---|---|---|
| Exo. TGF-β1 | 449±32 | 4.96±0.94 |
| Low Gp+exo. TGF-β1 | 495±89 | 6.04±0.33 |
| High Gp+exo. TGF-β1 | 492±28 | 6.87±3.07 |
| Low Gp+TGF-β1 | 470±79 | 4.87±0.74 |
| High Gp+TGF-β1 | 498±12 | 8.51±1.15 |

Trypsin -      Trypsin +

CARTILAGE MATERIAL HAVING MINIMAL HYPERTROPHY AND ROBUST INTEGRATION CAPACITY, AND USES THEREFOR

CROSS REFERENCE TO RELATED APPLICATIONS

This application claims the benefit of U.S. Provisional Patent Application No. 62/654,800, filed Apr. 9, 2018, which is incorporated herein by reference in its entirety.

Focal cartilage defect is a common and prevalent knee problem that affects people of all ages. Unfortunately, it is also a major clinical challenge in orthopedics, as articular cartilage is avascular with very limited intrinsic self-healing ability. If left untreated, these cartilage defects could eventually lead to the onset of osteoarthritis (OA), with total joint replacement as the final solution.

Mesenchymal stem cells (MSCs) represent a promising cell source to regenerate cartilage owing to their relatively easy isolation and robust chondrogenesis upon stimulation. However, under current culture conditions such as pellet culture, MSCs often undergo concomitant hypertrophy with chondrogenesis, resulting in inferior fibro-cartilage or calcified cartilage formation.

In Dang, P. N. et al., "Driving Cartilage Formation in High-Denisty Human Adipose-Derived Stem Cell Aggregate and Sheet Constructs without Exogenous Growth Factor Delivery" Tissue Eng. Part A 2014 December; 20(23-24):3163-75, an MSC sheet is described, which forms a cartilaginous material, but as shown in FIG. 1 (reproduced from Dang, P. N. et al.), the described materials are far from optimal for use as a cartilage replacement, at least because the compressive modulus is at least two order of magnitude lower than native cartilage of the knee. Furthermore, those materials do not integrate well into native cartilage tissue and undergo hypertrophy followed by calcification, limiting their utility in cartilage repair and growth in patients.

SUMMARY

In one aspect, a method of preparing cartilaginous material is provided. The method comprises: culturing mesenchymal stem cells in vitro on a cell culture substrate past confluence to produce a tissue structure comprising mesenchymal stem cells (MSCs) and mesenchymal stem cell-derived extracellular matrix (mECM); contacting the MSCs in the mECM (MSC-mECM) with a cell dissociating agent in an amount and for a duration sufficient to cause rounding of the MSCs in the MSC-mECM; removing the dissociating agent from the MSC-mECM; and culturing the dissociating agent-treated MSC-mECM in chondrogenic media, to produce cartilaginous material.

In another aspect, a method of producing a cartilage material in a patient is provided. The method comprises implanting a cartilaginous material in an anatomical site in a patient. The cartilaginous material is prepared by: culturing mesenchymal stem cells in vitro on a cell culture substrate past confluence to produce a tissue structure comprising mesenchymal stem cells (MSCs) and mesenchymal stem cell-derived extracellular matrix (mECM); contacting the MSCs in the mECM (MSC-mECM) with a cell dissociating agent in an amount and for a duration sufficient to cause rounding of the MSCs in the MSC-mECM; removing the dissociating agent from the MSC-mECM; and culturing the dissociating agent-treated MSC-mECM in chondrogenic media, to produce cartilaginous material.

BRIEF DESCRIPTION OF THE DRAWINGS

FIG. 6A is a photograph showing the respective sizes of fused pellets and fused MSC-mECM after 4 weeks of chondrogenesis. Safranin O/Fast Green staining (FIG. 6B) at 4 weeks and Real time-PCR analysis (FIG. 6C) at 2 weeks and 4 weeks of fused pellets and fused MSC-mECM undergoing chondrogenesis with TGF-β3.

DETAILED DESCRIPTION

Figures 1, 2:
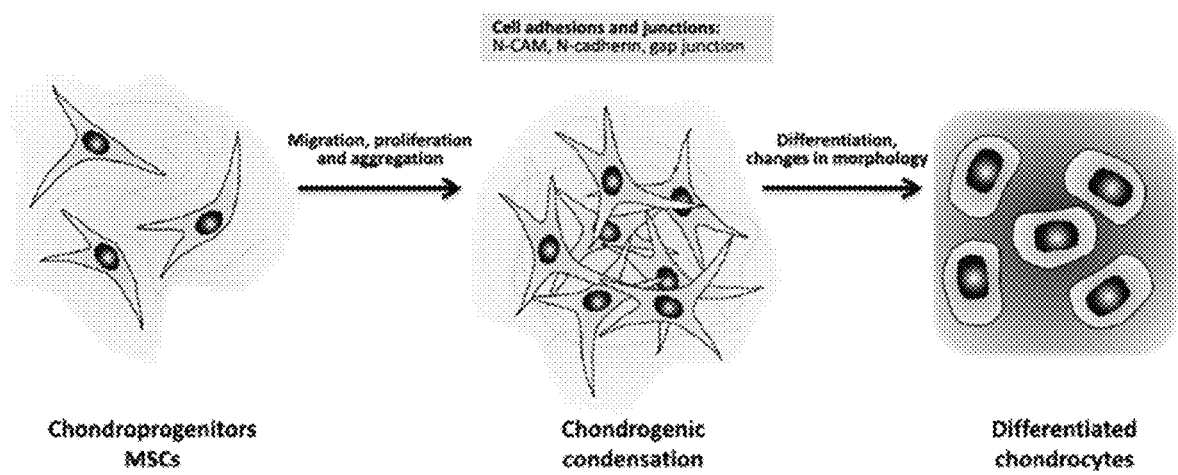
FIG. 1 is a table showing physical qualities of an MSC cell sheet as described in Dang, P. N. et al., Tissue Eng. Part A 2014 December; 20(23-24):3163-75.
FIG. 2 is a schematic diagram depicting chondrogenic condensation, reproduced in part from Richardson, S. M., et al. "Mesenchymal Stem Cells in Regenerative Medicine: Focus on Articular Cartilage and Invertebral Disc Regeneration" (2016) Methods 99:69-80.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values.

As used herein, the terms "right", "left", "top", "bottom", and derivatives thereof shall relate to the invention as it is oriented in the drawing Figures. However, it is to be understood that the invention can assume various alternative orientations and, accordingly, such terms are not to be considered as limiting. Also, it is to be understood that the invention can assume various alternative variations and stage sequences, except where expressly specified to the contrary. It is also to be understood that the specific devices and processes illustrated in the attached drawings, and described in the following specification, are examples. Hence, specific dimensions and other physical characteristics related to the embodiments disclosed herein are not to be considered as limiting.

As used herein, the terms "comprising," "comprise" or "comprised," and variations thereof, are meant to be open ended. The terms "a" and "an" are intended to refer to one or more.

As used herein, the "treatment" or "treating" of a condition, wound, or defect means administration to a patient by any suitable dosage regimen, procedure and/or administration route of a composition, device or structure with the object of achieving a desirable clinical/medical end-point, including repair and/or replacement of a damaged, defective, or malformed cartilage, such as hyaline cartilage or articular cartilage.

The term "patient" or "subject" refers to members of the animal kingdom including but not limited to human beings and "mammal" refers to all mammals, including, but not limited to human beings.

Cells may be terminally differentiated and/or progenitor cells. Cells progress (differentiate) through lineage beginning from progenitor cells, such as stem cells, including pluripotent cells (iPSCs), and along a lineage of multipotent progenitor cells, oligopotent progenitor cells, to unipotent cells or tissue specific cells such as chondrocytes. Mesenchymal stem cells (MSCs) are multipotent progenitor cells found in adult mesenchymal tissue, including, without limitation, bone marrow, umbilical cord blood, muscle, and adipose tissue. Adipose tissue is an abundant source of MSCs, and can be readily obtained from a patient by lipoaspiration (e.g., liposuction).

Mesenchymal stem cells (MSCs) can be obtained from a variety of tissues according to established methods known to those of ordinary skill in the art. Non-limiting examples of MSCs include: bone marrow-derived mesenchymal stem cells, adipose-derived mesenchymal stem cells, umbilical cord blood-derived mesenchymal stem cells, umbilical cord matrix-derived mesenchymal stem cells, hamstring tendon-derived mesenchymal stem cells, bone-derived mesenchymal stem cells, muscle-derived mesenchymal stem cells, or synovium-derived mesenchymal stem cells. MSCs may also be generated from induced pluripotent stem cells (iPSCs), which are derived from somatic cells, such as skin or blood cells, that have been reprogrammed back into an embryonic-like pluripotent state (see, e.g., Singh V K, et al., Induced pluripotent stem cells: applications in regenerative medicine, disease modeling, and drug discovery. *Front Cell Dev Biol.* 2015; 3:2; Diederichs S, Tuan R S. Functional comparison of human-induced pluripotent stem cell-derived mesenchymal cells and bone marrow-derived mesenchymal stromal cells from the same donor. *Stem Cells Dev.* 2014 23:1594-610). In one embodiment, the MSCs are adipose-derived mesenchymal stem cells. In another embodiment, the MSCs are bone marrow-derived mesenchymal stem cells.

In one non-limiting example, MSCs can be obtained from adipose tissue according to the following. Adipose tissue, e.g., lipoaspirated adipose tissue, is collected and washed, e.g., in saline. The tissue is then centrifuged or settled to separate the tissue from free lipids and from aqueous wash. The adipose tissue is then treated/digested with a proteinase, such as collagenase, to dissolve the extracellular matrix (ECM), and to release individual cells. Alternatively, and avoiding enzymatic digestion, the fat tissue can be vibrated (e.g., 6,000 vibrations per minute) to release cells from the tissue. The digested or shaken tissue optionally can be filtered. The tissue is then centrifuged to separate the stromal vascular fraction (SVF), comprising adipose-derived stem cells, from adipocytes (see, e.g., Rasposio, E, et al. "Adipose-derived stem cells: Comparison between two methods of isolation for clinical applications" *Ann Med Surg (Lond)* 2017 August; 20: 87-91).

The SVF can be used directly as an enriched source of MSCs or can be cultured and optionally stored. MSCs are among cells in the SVF that adhere to plastic, such as a typical tissue culture dish or flask. As such, the cells may be cultured for a suitable time in suitable medium to support growth of the MSCs (available, e.g., commercially, e.g., MESENCULT™ products, from Stem Cell Technologies, Inc. of Cambridge, Mass.), and the enriched MSC population is cultured under non-differentiation conditions. MSCs can be removed from the culture vessel by typical tissue culture methods and can be seeded on a cell culture surface in any cell culture medium able to support an MSC culture. Media useful for growth and expansion of MSC cultures are broadly-known and are available from many commercial sources.

Extracellular matrix (ECM) refers to the non-cellular component present within all tissues and organs. It also can be produced by cultured cells, for example, cells cultured past confluence and in the presence of an enhancing agent, such as ascorbic acid. As used herein, a confluent cell culture means 100% of a cell culture surface, such as the bottom of a culture dish, is covered by cells, leaving no further room for cells to grow as a monolayer. As such, post-confluence refers to a cell culture in which the cells are past confluence (past 100% confluence) and often forms a multi-layered or three-dimensional (3D) structure. Ascorbic acid can be utilized to enhance production and deposition of ECM in the cell culture. In the context of the present disclosure, MSCs cultured in the presence of ascorbic acid form a three-dimensional structure.

Medium (pl. media), such as cell culture medium or cell growth medium, is a liquid or gel designed to support growth of cells. A large variety of media suitable for cell growth are known and are commercially available, e.g., for growth and propagation of stem cells, such as MSCs, or for their differentiation into cartilage cells (or chondrocytes), or chondrogenesis. A cell growth medium may comprise supplements, such as serum, antibiotics and other therapeutic agents, vitamins, cytokines, growth factors, etc., though for certain uses, such as production of cartilage for use in humans, serum, particularly xenogeneic serum, such as fetal bovine serum, may be avoided, and serum-free media may be best suited for that purpose. Other ingredients that may create unwanted toxicity or immune response may be avoided for use in production of implantable materials.

In one embodiment, chondrogenic medium comprises one or more chondrogenic growth factors and/or ingredients that support chondrogenesis. Non-limiting examples of chondrogenic growth factors include transforming growth factor beta-1 (TGF-β1), transforming growth factor beta-3 (TGF-β3), bone morphogenetic protein 2 (BMP2), bone morphogenetic protein 6 (BMP6), growth differentiation factor 5 (GDF5), or fibroblast growth factor 18 (FGF18). In one embodiment, the chondrogenic growth factor is TGF-β3.

Chondrogenesis occurs as a result of mesenchymal cell condensation and chondroprogenitor cell differentiation. As described herein, chondrogenesis occurs by way of the condensation and differentiation of MSCs in chondrogenic medium, optionally comprising a chondrogenic growth factor. Chondrogenic medium is broadly-known and is commercially available from a variety of sources. Non-limiting examples of chondrogenic medium includes MesenCult™-ACF Chondrogenic Differentiation Medium (Stemcell Technologies, Inc.) or Chondrocyte Differentiation Medium (Lonza).

As used herein, a "dissociating agent" is a compound or composition that can partially or fully dissociate or detach cells from its associated ECM in a tissue, organ, or, in the context of the present disclosure, a post-confluent cell culture. Under the condition of partial dissociation, cells adapt a round morphology but still attach to the substrate, such as ECM. A variety of cell dissociating agents are known to those of skill in the art, including, without limitation, proteases (or proteinases) and chelating agents. Non-limiting examples of proteases include trypsin, collagenase, elastin, pepsin, and papain. Non-limiting examples of chelating agents include: EDTA (ethylenediaminetetraacetic acid) and EGTA (ethylene glycol-bis(β-aminoethyl ether)-N,N,N',N'-tetraacetic acid). In one example, a common cell dissociating agent is trypsin-EDTA, e.g., 0.25% trypsin, 0.02% EDTA. In the context of the non-dissociative treatment of a cell structure as described herein, the amount of protease or chelating agent used to treat the cell structure may be much lower than is typically used to disrupt a cell monolayer culture for cell passaging.

A method of producing a cartilaginous material, e.g., prosthetic cartilage, is provided. The composition produced by the method is a live, cell-including, (generated by autologous or allogenic stem cells), prosthetic cartilaginous material that can be used for generation, repair, regeneration, or replacement of cartilage, and which may eventually mature into normal/healthy articular cartilage. The cartilaginous material prepared by the described method is superior to existing sheet or pellet methods in that the resultant product exhibits an enhanced mechanical property close to native cartilage (indicated by the results from mechanical testing), lower hypertrophic phenotype and therefore lower potential for ossification, that is lower risk of producing osteoarthritic conditions. Further, the cartilaginous material prepared by the described method better integrates into existing cartilage as compared to prior materials and exhibits superior physical qualities. As such, as compared to prior methods, the method described herein produces a superior product for use in generation, repair, regeneration, or replacement of cartilage.

The method includes preparation of a tissue structure comprising MSCs. The tissue structure is prepared by culturing MSCs in suitable stem cell growth medium past confluence to produce a tissue structure comprising cells and ECM (mesenchymal stem cell-derived extracellular matrix (mECM), with the combination of MSCs and mECM being referred to herein as MSC-mECM). For robust generation of mECM by the MSCs, ascorbic acid may be added to the culture medium. The tissue structure is then treated with a cell dissociating agent, such as a protease and/or a chelating agent, e.g., trypsin-EDTA as it is commonly known in the cell culture field, to cause rounding of the cells within the tissue structure, but not dissociation or separation of the cells from the mECM. That is, the cells are treated with an amount of the dissociating agent and for a duration such that the cells are rounded but are substantially or completely retained within the mECM. This is referred to herein as a "non-dissociating" treatment of the tissue structure (MSC-mECM) with the cell dissociating agent.

After the partially-dissociating treatment of the tissue structure with the cell dissociating agent, the tissue structure is then cultured in chondrogenic medium. Prior to culture in chondrogenic medium, the dissociating agent is removed from the tissue structure, for example, the dissociating agent in solution is aspirated and the tissue structure is washed or cultured in medium, phosphate-buffered saline, or any suitable wash solution, and the tissue structure may be allowed to recover, e.g., for from 1-24 hours, such as overnight, in suitable cell growth medium such as the stem cell growth medium used to produce the tissue structure. The tissue structure (MSC-mECM) is then cultured in chondrogenic medium to produce a cartilaginous material. Chondrogenic medium may comprise one or more chondrogenic growth factors, such as TGF-β3, and/or one or more additional chondrogenic growth factors. The tissue structure is grown for from 1 day to 2 months, e.g., 1, 2, 3, 4, 5, 6, 7, or 8 weeks, or longer, in the chondrogenic medium to produce cartilaginous material, and can be implanted in a patient at any suitable point.

As can be seen in Example 2, below, the MSCs are cultured in a normoxic or hypoxic atmosphere when depositing the mECM. Afterwards, the MSC-mECM is cultured in the chondrogenic medium in a normoxic or hypoxic atmosphere, undergoing chondrogenesis and forming cartilage. Hypoxic conditions are conditions at which oxygen levels are lower than in a cell culture in a normoxic atmosphere comprising from 20% to 23% oxygen. Depending on the cell culture method used during preparation of the MSC-ECM and chondrogenesis, the percent or partial pressure of dissolved oxygen present in the cell culture medium should approximate that of the gaseous atmosphere in which the culture is maintained (e.g., Henry's law). However, the oxygen levels in the culture medium in which the cells are grown and differentiated should approximate those of an atmosphere, such as that of a tissue culture incubator, in which a cell culture is maintained. As such, for normoxic (during mECM generation)/normoxia (during chondrogenesis) conditions, the dissolved oxygen ranges from 20% to 23% of the total dissolved gases in tissue culture media. In hypoxic/hypoxia conditions, the dissolved oxygen is lower than in normoxic/normoxia conditions, with the oxygen being replaced by another gas, such as nitrogen. Hypoxic conditions are therefore where the partial pressure of oxygen in a culture medium relative to all dissolved gasses in the culture medium, is less than 20%, 10% or lower, or ranges from 1% to 5% of the total dissolved gas content in the culture medium, for example, from 1% to 3%, or is 2% of the total dissolved gas content in a culture medium.

In aspects, a method of producing a cartilage material in a patient is provided. The method comprises implanting in an anatomical site in the patient a cartilage material prepared according to any embodiment of the methods for making cartilage material as described herein. The anatomical site is any location in the patient where cartilage repair is needed. For example, the location of cartilage injury, damage, insufficiency, deficiency or defect in the patient may be a site of articular or hyaline cartilage injury, damage, insufficiency, deficiency or defect in the patient. For such treatment methods, it may be desirable to use the patient's own (autologous) MSCs to prepare the MSC-mECM used to generate the cartilage material, though allogeneic or xenogeneic MSCs may be used in certain circumstances and conditions.

EXAMPLES

FIG. 2 depicts the process of chondrogenesis, depicting the condensation of chondrogenic progenitors to form cartilage, which has not been reported in other methods. As shown in FIG. 1, one example of current technology is limited at least because the compressive modulus is at least two orders of magnitude lower than native cartilage of the knee. Also, integration of the engineered cartilage tissue is limited, and the prior tissue constructs are susceptible to hypertrophy followed by calcification, e.g., as described in the Examples below. The methods described herein generate a cartilage tissue that overcomes these limitations.

Example 1

Material & Methods

Figure 3:
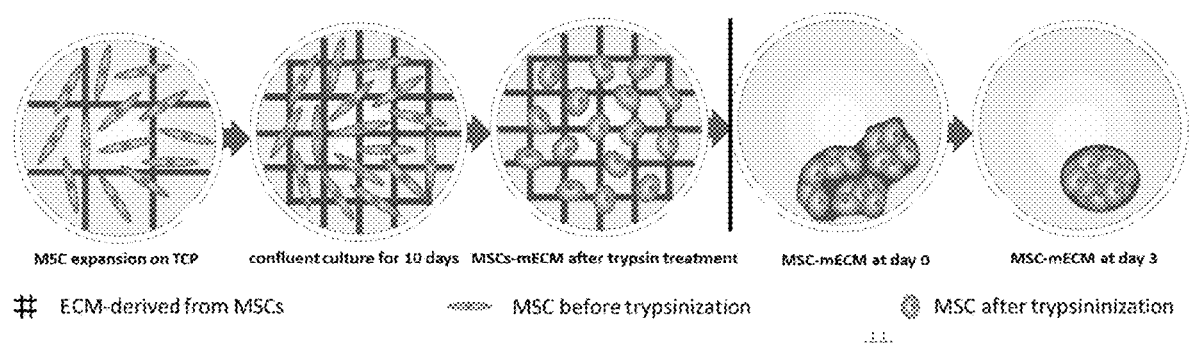
FIG. 3. MSCs were cultured under confluent condition for 10 days to deposit extracellular matrix (mECM), which served as scaffold for cartilage formation. Afterwards, the MSC-impregnated mECM (MSC-mECM) was briefly treated with trypsin, which allowed MSCs to adopt a round morphology without being detached from their own mECM. Afterwards, constructs were subjected to condensation and chondrogenesis, finally forming cartilage tissue.

FIG. 3 depicts the overall scheme of the present methods. Human bone marrow-derived MSCs (hBMSCs) were isolated from surgical waste.

Generation of MSC-derived ECM: MSCs were seeded on tissue culture plates (TCP) at a density of 10,000 cells/cm$^2$ and cultured in MSC growth medium (GM, α-MEM containing 10% fetal bovine serum (FBS, Invitrogen, Carlsbad, Calif., USA), 1% antibiotics-antimycotics (Life Technologies, Carlsbad, Calif., USA), and 1.5 ng/ml FGF-2 (RayBiotech, Norcross, Ga., USA)) until 100% confluence. Afterwards, FGF-2 was withdrawn and 50 µg/mL L-ascorbic acid phosphate (Sigma-Aldrich, St. Louis, Mo., USA) was supplemented into GM for another 10 days. The medium was changed every 2 days.

Chondrogenesis of MSC-mECM: After 10 days, cultures were subjected to a pre-trypsinization process. Briefly, 0.25% trypsin-EDTA (Invitrogen) was incubated with the culture (~2.5 minutes), until the cells were seen to adopt a round morphology but remain attached to the ECM as observed under the microscope. Afterwards, trypsin treatment was terminated by adding GM. This group was named as "trypsin+" and the control group without trypsinization was designated as "trypsin–". MSC-mECM, from both groups, were detached by gentle agitation and transferred to the well of a 48-well culture plate. They were cultured in full chondrogenic medium (DMEM, 40 µg/mL proline (Sigma-Aldrich), 100 nM dexamethasone (Sigma-Aldrich), 1% antibiotics-antimycotics, 50 µg/mL L-ascorbic acid (Sigma-Aldrich), 1×Insulin-Transferrin-Selenium (Life Technologies) and 10 ng/mL transforming growth factor-β3 (TGFβ3) (Peprotech, Rocky Hill, N.J., USA)) up to 28 days, with medium changed every 2 days. The chondrogenesis was analyzed with real-time PCR, Glycosaminoglycan Assay (GAG assay), and histology.

Real-time PCR: Total RNA of the cultures was extracted with TRIZOL reagent (Invitrogen) and purified using RNeasy® Plus Mini Kit (Qiagen, Germantown, Md., USA). Reverse transcription was performed using SuperScript® VILO™ cDNA Synthesis Kit (Invitrogen) according to the manufacturer's protocol. Real-time PCR was performed using the SYBR Green Reaction Mix (Applied Biosystems, Life Science, Foster City, Calif., USA) with a StepOne-Plus thermocycler (Applied Biosystems). Gene expression levels of collagen type IIA1(COL2A1), aggrecan, collagen type IA2(COL1A2), collagen type X, alkaline phosphatase (ALP) and matrix metalloproteinase 13 (MMP13) were analyzed. All gene expression levels were determined using the $2^{-\Delta\Delta Ct}$ method and normalized to that of human 18S rRNA as a housekeeping gene standard.

Biochemical analyses: Total GAG deposited within the in vitro engineered cartilage was measured. Constructs were homogenized and then digested for 18 hours in a papain solution (125 µg/ml papain, 50 mM sodium phosphate buffer, 2 mM N-acetyl cysteine (Sigma-Aldrich), pH 6.5) at 500 µl/construct. An aliquot of the digest was assayed for sGAG content using the dimethylmethylene blue dye binding assay (Blyscan, Biocolor, United Kingdom) according to the manufacturer's instruction. dsDNA was quantified with another aliquot of the digest using PicoGreen based assay. All assays were performed in triplicate.

Histology: Cultures were fixed in 4% paraformaldehyde (Fisher) at 4° C. overnight and dehydrated with an ethanol gradient series, followed by clearing with xylene and embedding in paraffin. Histological sections (7 µm thickness) were stained with Safranin O solution (Sigma-Aldrich) to detect sGAG with Fast Green as a counterstain or Alizarin red solution to detect calcium deposition.

Pellet culture of MSCs (control group): Conventional pellet culture was employed as control, since they were able to form a construct with a similar mechanical strength to native cartilage. Briefly, hMSCs were suspended into full chondrogenic medium at a final density 1×10$^6$/ml. 250 µl of cell suspension was added into individual wells of conical-bottom 96-well plates (NUNC; Sigma-Aldrich), and centrifuged at 300×g for 10 min. They were maintained in full chondrogenic medium up to 28 days, with medium changed every 2 days.

In vitro fusion of MSC-mECM and MSC-pellet: Individual MSC-pellets and MSC-mECMs were first made as described above. They were cultured in full chondrogenic medium for another 5 days and then placed into the cylindrical void space in a silicone gel mode. In order to enhance the fusion and allow the medium diffusion, a stainless-steel mesh was used to cover both sides. The constructs, together with the silicon mode and mesh, were cultured in a rotating bioreactor (Synthecon, Houston, Tex., USA) for 4 weeks. Full chondrogenic medium was changed every 2 days.

In vitro repair using cartilage explant from bovine: Bovine full thickness articular cartilage was harvested from femoral condyle of adult calves. 8 mm in diameter cartilage discs with a 3 mm in diameter cylinder shaped defect in the middle were cut out with clean biopsy punches and balanced in full chondrogenic medium for 48 hours. The bovine explant defects were filled with either MSC-pellet or MSC-mECMs and cultured in rotating bioreactor with full chondrogenic medium for 4 weeks. Medium was changed every 2 days. After 4 weeks of culture, medium was changed to explant culture medium (DMEM containing 2% fetal bovine serum (FBS, Invitrogen, Carlsbad, Calif., USA), 1% antibiotics-antimycotics (Life Technologies, Carlsbad, Calif., USA), 50 µg/mL L-ascorbic acid (Sigma-Aldrich)) for another 2 weeks. Medium was changed every 2 days.

Mechanical testing: To examine the integration of implants into explant, a push-out test was used (Tissue Eng Part A. 2014 September; 20(17-18):2402-11. Cartilage tissue engineering application of injectable gelatin hydrogel with in situ visible-light-activated gelation capability in both air and aqueous solution.) A plunger was used to push the implants out and the applied forced was recorded. The maximal force during the test was used. The higher force suggested better integration.

PNA staining: MSC-pellet or MSC-mECM cultured were collected after 0, 1, 3, 5 days of chondro-induction. They were embedded into paraffin as described above. The sections were deparaffinized and rehydrated before antigen retrieval with hot ddH$_2$O. The sections were then stained with 1:1000 PNA (Sigma-Aldrich) solution and 1:3000 diluted DAPI (Thermal Fisher Scientific, Waltham, Mass., USA).

Western blot of N-cadherin: The extent of mesenchymal condensation in MSC-pellet and MSC-mECM was analyzed by assessing the level of the cell adhesion molecule, N-cadherin, as a marker of cell-cell interaction. MSC-pellets and MSC-mECMs were cultured in full chondrogenic medium, and protein extracts at day 0, 1, 3, 5 were prepared using RIPA buffer (Sigma-Aldrich). After reducing SDS-PAGE, protein blots were performed using low fluorescence background polyvinylidene fluoride membranes (Millipore, Billerica, Mass., USA), blocked in 3% milk in TBS-T (0.25% Tween-20 in TBS) for 1 hour, and probed overnight at 4° C. with various antibodies (GAPDH, N-cadherin (Cell Signaling Technology, Danvers, Mass. USA)) in 1% milk/TBS-T. Immunodetection was performed with HRP-conjugated secondary antibodies (Thermo Scientific, Waltham, Mass., USA), followed by chemiluminescent HRP substrate (Thermo Scientific), and imaged with a Fotodyne/Analyst FX CCD camera system (FOTODYNE Incorporated, Hartland, Wis., USA).

In vivo subcutaneously implantation to examine the osteogenic potential: Female Severe Combined Immunodeficiency (CB17/Icr-Prkdcscid/IcrIcoCrl SCID®) mice (8-12 weeks old; Charles River Laboratories; Wilmington, Mass.) were used to assess the osteogenic potential of in vitro engineered cartilage. Fused MSC-mECMs were prepared according to the procedures described above. After 2 weeks of in vitro culture, they were implanted subcutaneously into SCID mice for another 2 weeks. The constructs were harvested, and histological analysis were used to estimate the deposition of GAG.

Statistical analysis: All data from control and experimental groups were analyzed using the unpaired Student's t-test or two-way ANOVA, with statistical difference set as p<0.05. All values were presented as mean±standard deviation.

Results

Figure 4:
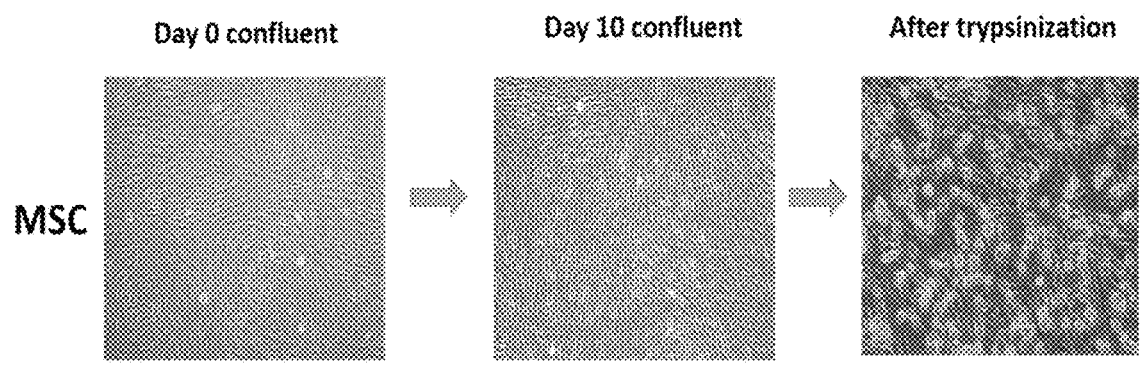
FIG. 4. Microscopic images of MSC-mECM at day0 of confluence, 10 days after confluence and right after brief trypsin treatment.
Figure 5A:
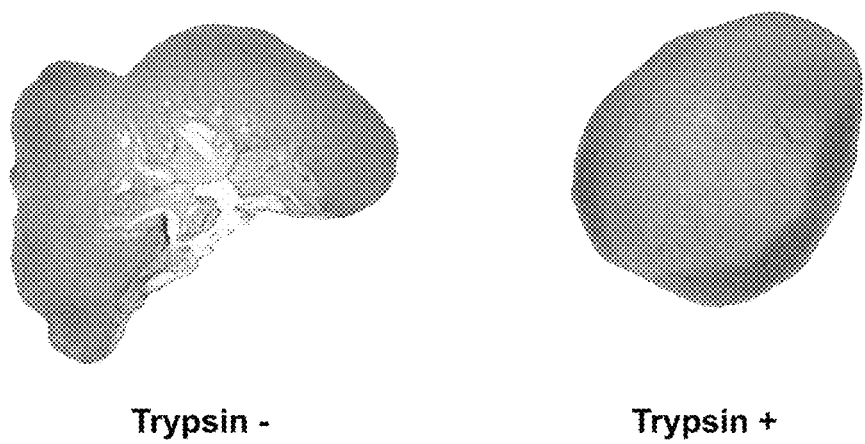
FIG. 5A shows Safranin O/Fast Green staining of cell sheets produced without (left) and with (right) partial trypsinization prior to culture for 21 days in chondrogenic medium, showing superior chondrogenesis in the cell sheet produced with a trypsinization pre-treatment step.
Figure 5B:
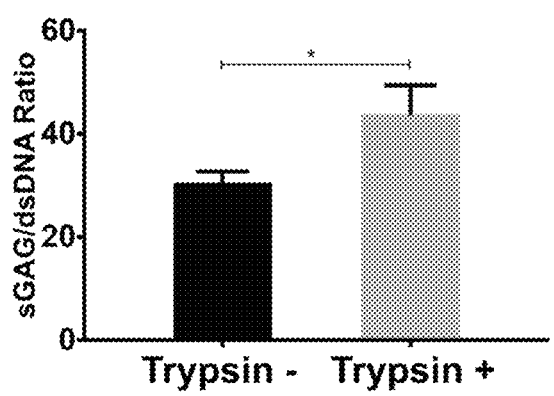
FIG. 5B shows sulfated glycosaminoglycan (sGAG)/dsDNA ratios for Trypsin− and Trypsin+ samples.
Figure 5C:
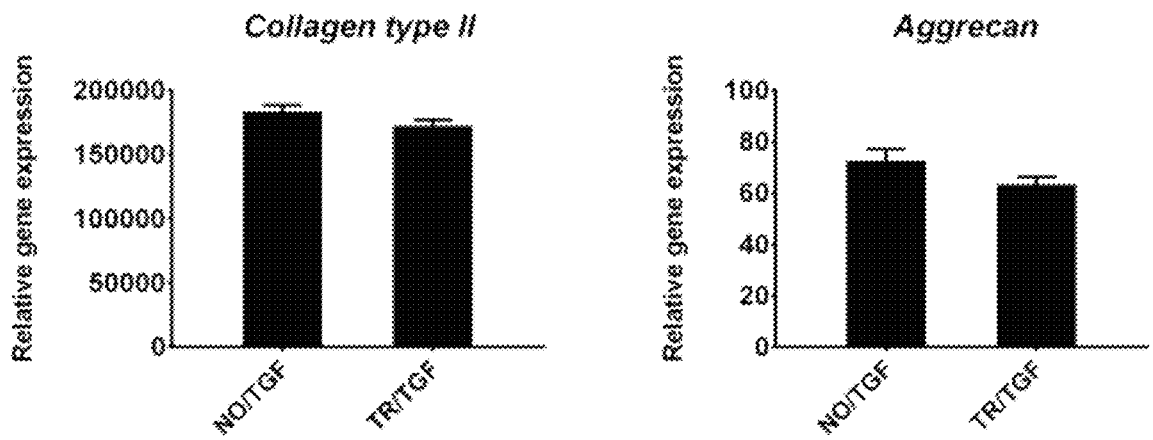
FIG. 5C shows real time PCR assay results of MSC-mECM without (NO/TGF) or with (TR/TGF) trypsin treatment undergoing chondrogenesis with TGF-β3 for 21 days.

MSCs growing on TCP for 10 days after confluence were briefly trypsinized, or not (TR or NO), and both MSCs and their deposited ECM were folded into MSC-mECM (FIG. 4). The constructs were then treated with or without TGF-β3 (NO or TGF) for 21 days. Trypsinized MSC-mECM with TGF-β3 treatment (TR/TGF) showed more compact structure with more uniformly distributed sGAG (FIG. 5A), and superior sGAG/dsDNA ratios for Trypsin- and Trypsin+ samples (FIG. 5B). Gene expression results showed comparable chondrogenic gene expression (collagen Type II and Aggrecan) in the NO/TGF and TR/TGF groups (FIG. 5C), indicating that trypisinization did not affect MSC chondrogenesis.

Figure 6A:
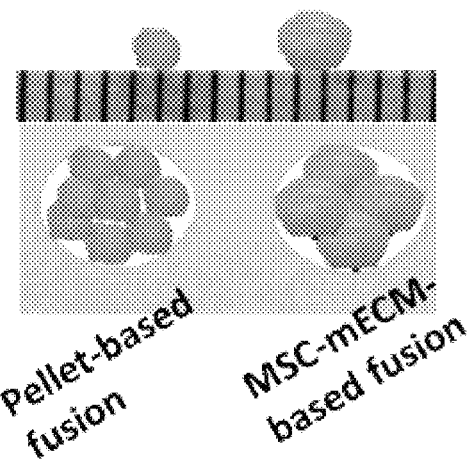
FIGS. 6A-6C.
Figure 6B:
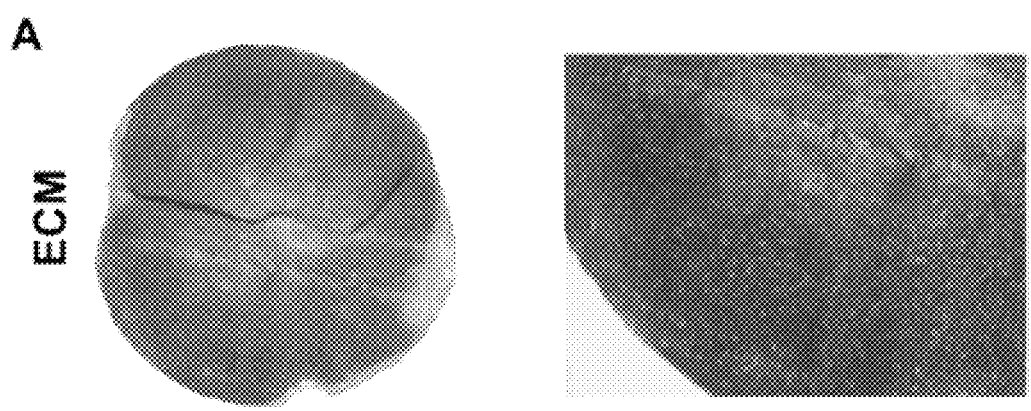
Figure 6B:
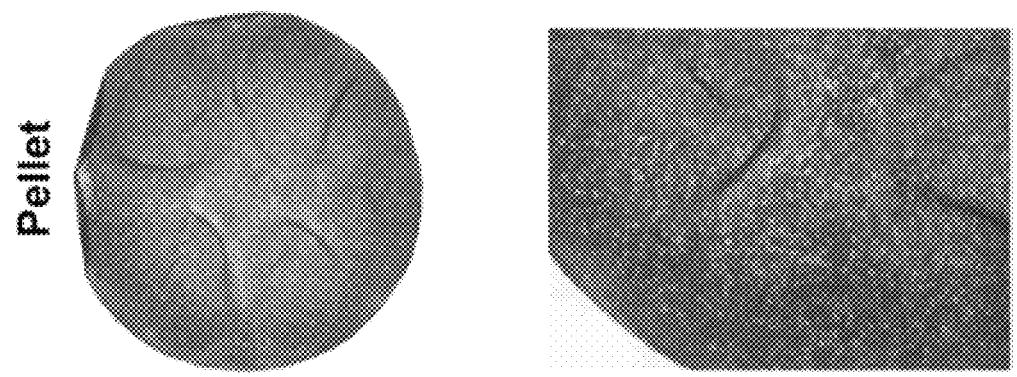

The chondrogenesis of fused MSC-mECM was then estimated by chondroinduction for 4 weeks with traditional MSC pellets as control. Both groups displayed uniformly distributed sGAG. The MSC-mECM group produced larger and more cohesive structures at 4 weeks (FIGS. 6A and 6B).

Figure 6C:
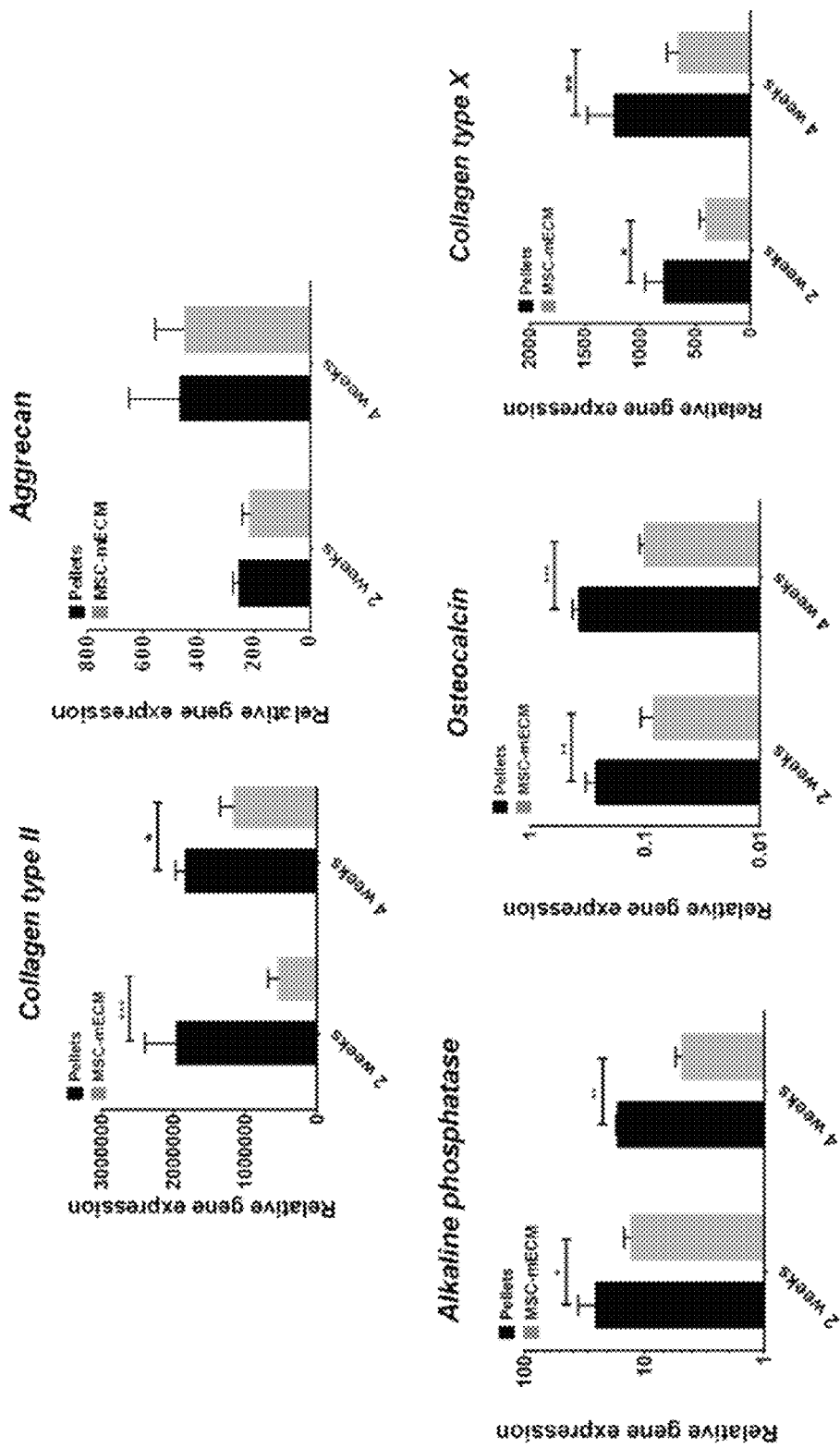

Gene expression showed that MSC-mECM group had comparable levels of chondrogenic gene expression (collagen type II and aggrecan) but much lower hypertrophic gene expression (alkaline phosphatase, osteocalcin, and collagen type X) (FIG. 6C).

Figure 7:
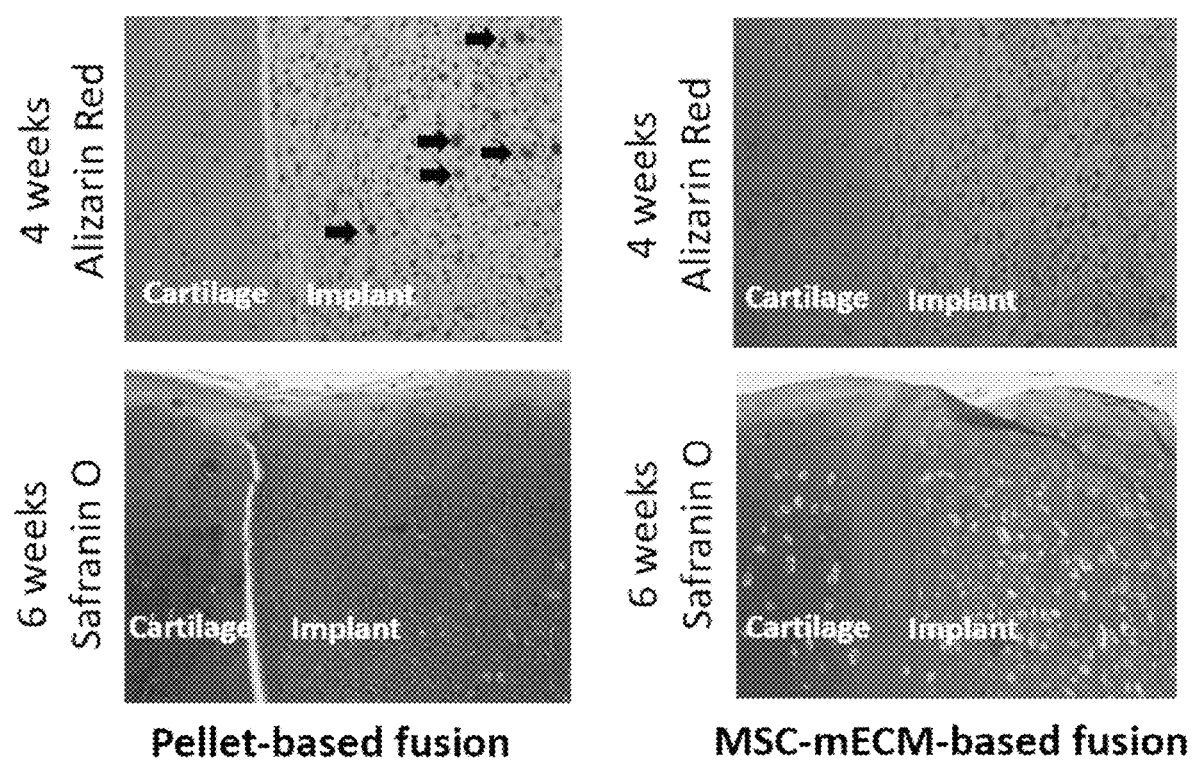
FIG. 7 provides photomicrographs showing Alizarin red staining (top) and Safranin O/Fast Green staining (bottom) of MSC-mECM group (right) or MSC pellet group (left) and explants at the indicated time points.
Figure 8A:
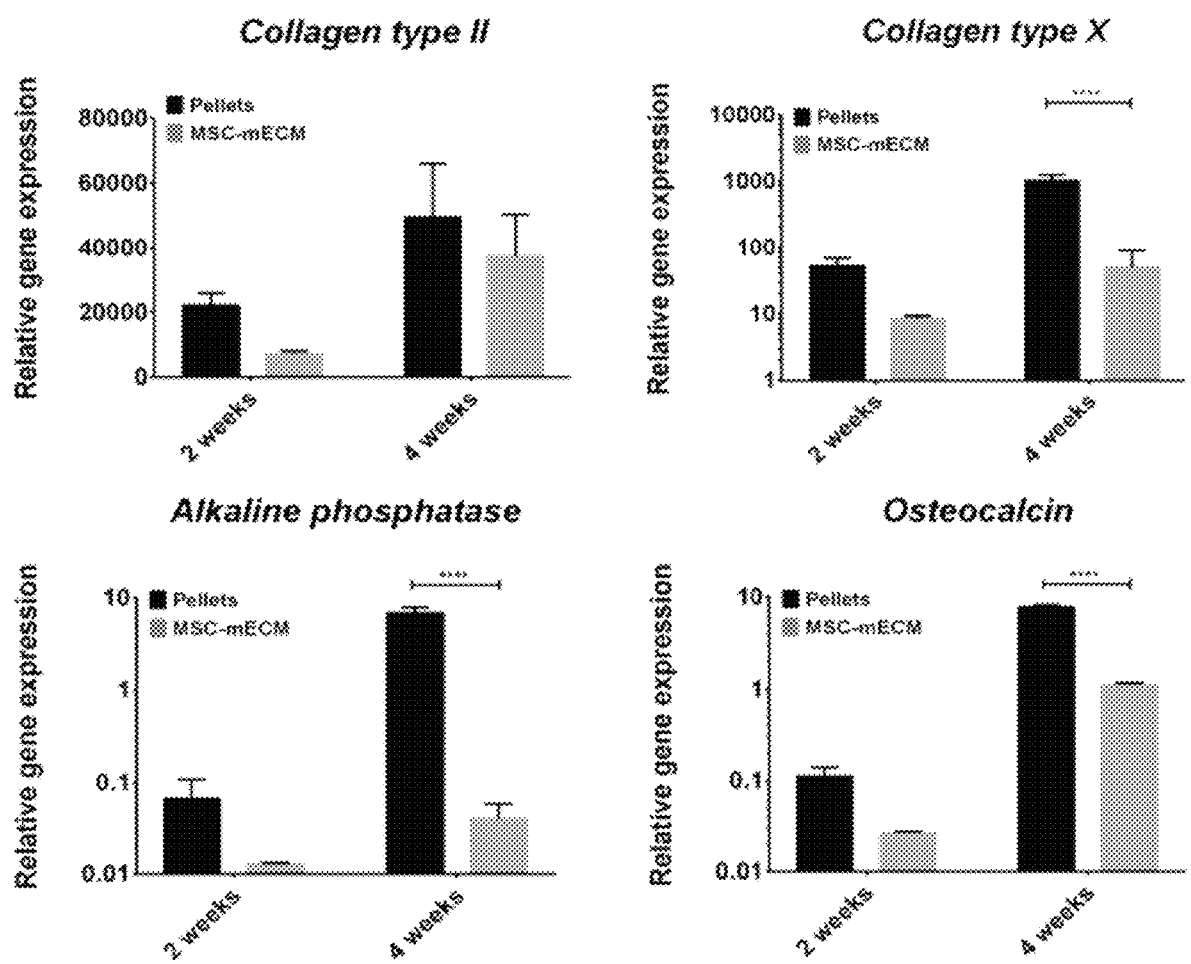
FIG. 8A. Real time PCR analysis of relative gene expression in MSC-mECM and MSC pellet groups at 2 weeks and 4 weeks of integration test between host tissue and fused MSC-mECM or fused pellets.
Figure 8B:
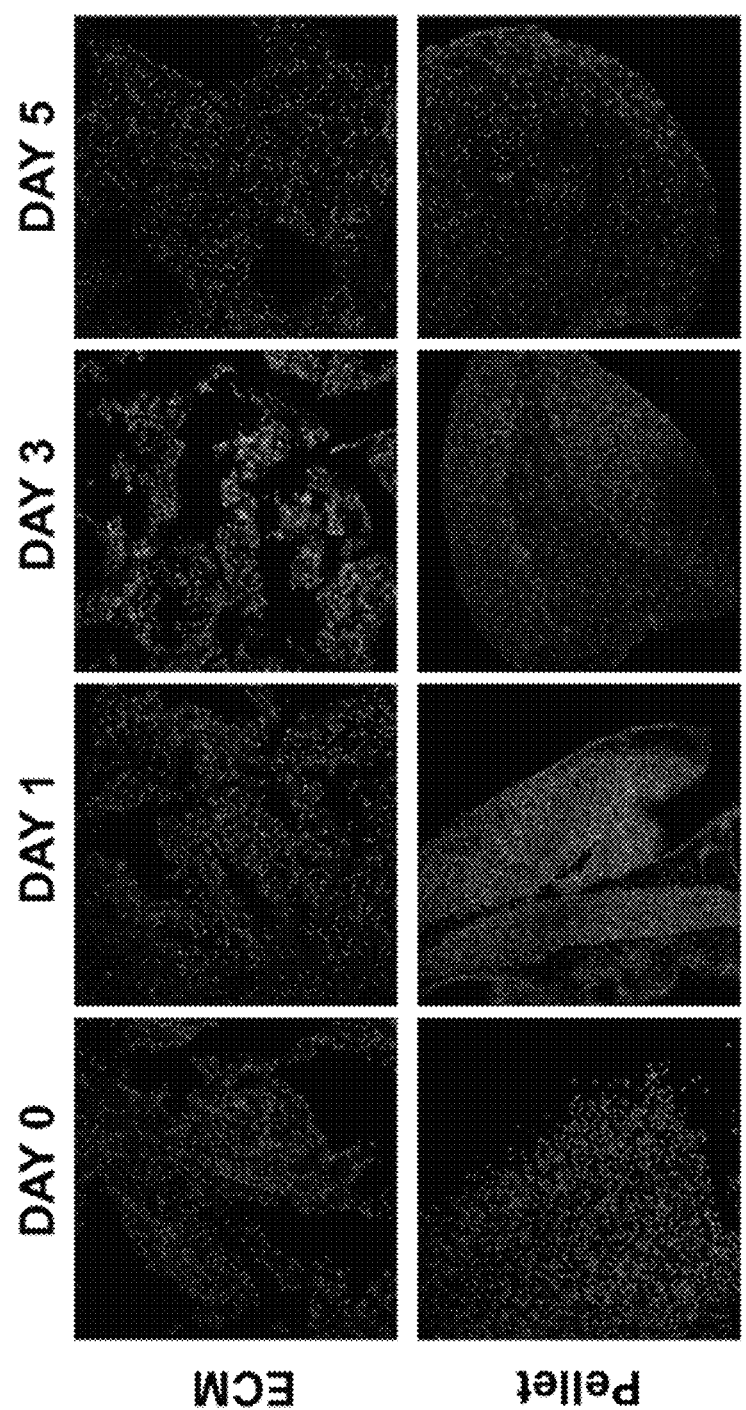
FIG. 8B provides exemplary photomicrographs showing PNA staining, illustrating progression of chondrogenic condensation in the MSC-mECM (ECM) and pellet groups.

For integration, a bovine cartilage explant model was used, with fused MSC-mECM or pellets to fill in the defect. After 4 weeks of culture, MSC-mECM showed better integration with host cartilage tissue (more connectivity with less open space between implant and native cartilage) and less calcification compared with pellet group (FIG. 7, top right). At 6 weeks of culture, as can be seen in FIG. 7, bottom right, integration is excellent in MSC-mECM group, with significantly higher binding force (450 kPa vs 300 kPa in pushout test). Gene expression showed MSC-mECM group had comparable chondrogenic gene expression, but much lower hypertrophic gene expression compared with MSC pellet group (FIG. 8A). The glycan moiety to which peanut agglutinin (PNA) binds is a known marker for pre-cartilage mesenchymal condensations and therefore PNA staining is often used to assess the condensation of MSCs. PNA staining of the pellet group and the MSC-mECM group depicted different temporal progression of condensation and chondrogenesis (FIG. 8B).

Figure 8C:
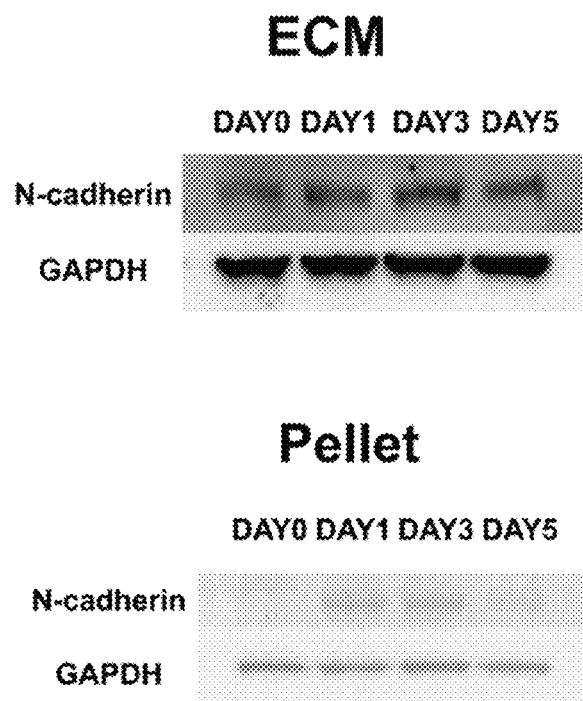
FIG. 8C provides Western Blots depicting N-cadherin expression in MSC-pellet and MSC-mECM explants.

Since the constructs from MSC-mECM went through a contraction and cell aggregation process that was similar to the developmental condensation process, we thus first performed PNA staining and N-Cadherin western blot to characterize condensation process. As shown in FIG. 8B, MSC-pellets showed a very rapid and strong PNA staining on day 1, which disappeared on day 3. While in MSCs-mECM group, PNA staining was weak on day 1, increased and reached peak on day 3 and then vanished on day 5. N-cadherin expression displayed a similar trend (FIG. 8C). Therefore, MSCs underwent different condensation patterns in these two culture conditions.

Figure 8D:
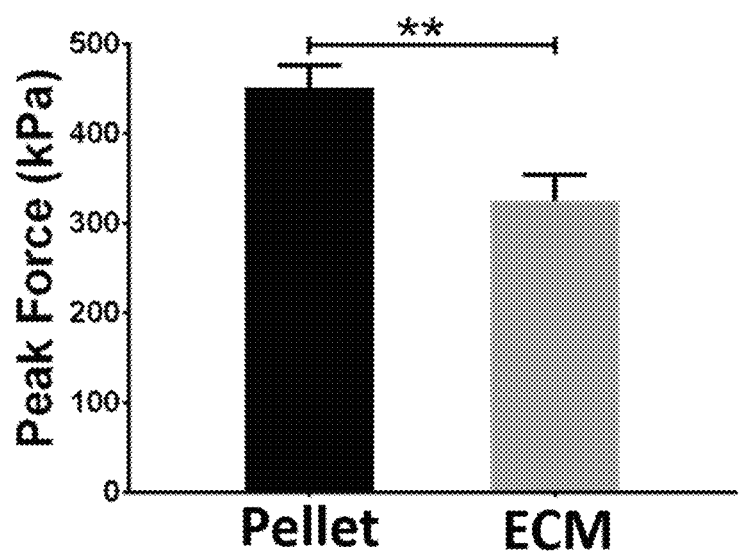
FIG. 8D provides a graph showing mechanical testing of MSC-pellet and MSC-mECM explants.
Figure 9:
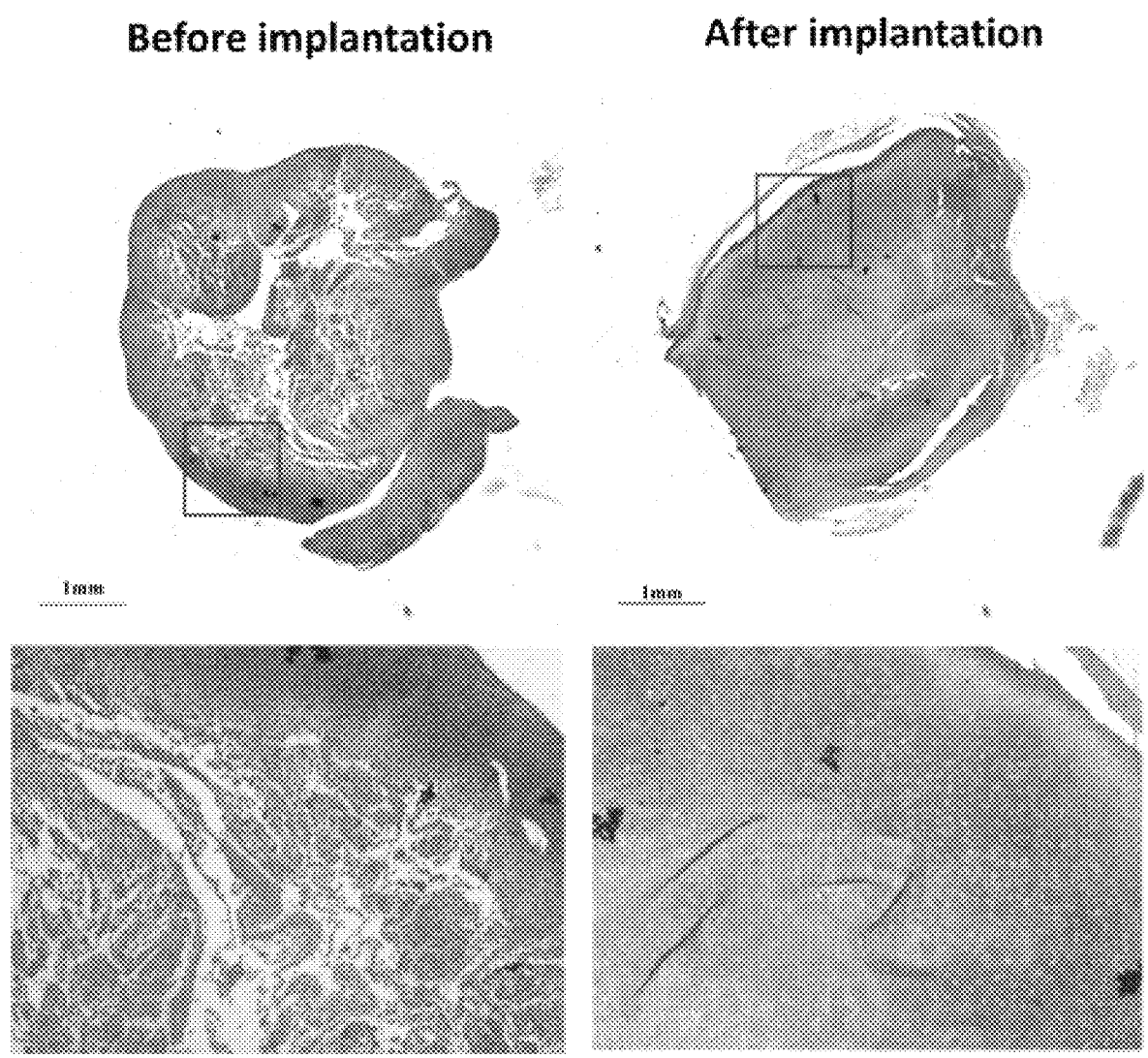
FIG. 9 provides photomicrographs of Safranin O/Fast Green staining of sGAG before and after subcutaneous implantation in SCID mice for 14 days.
Figure 10A:
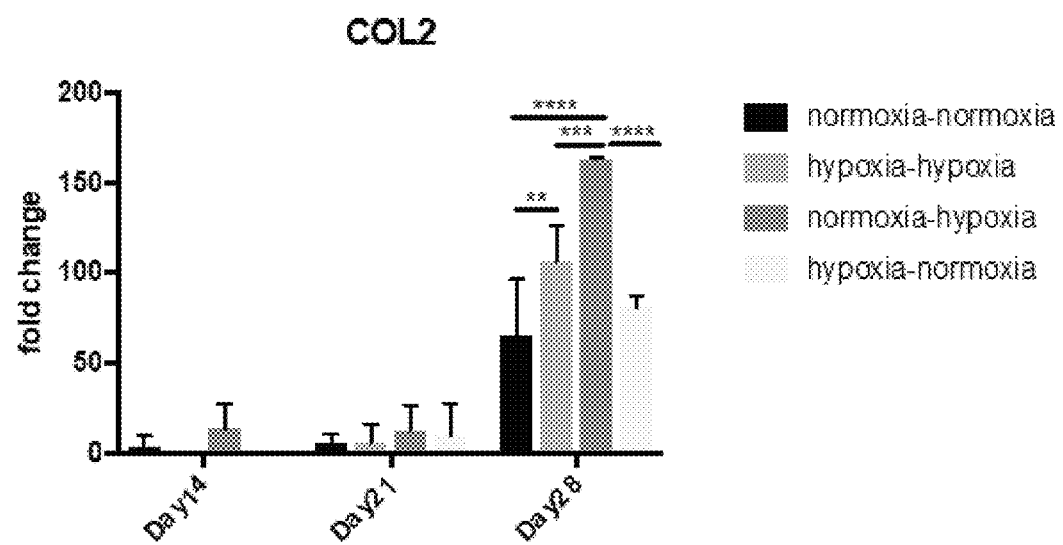
FIGS. 10A-10E are graphs providing RT-PCR data for cells cultured under conditions described in Example 2.
Figure 10B:
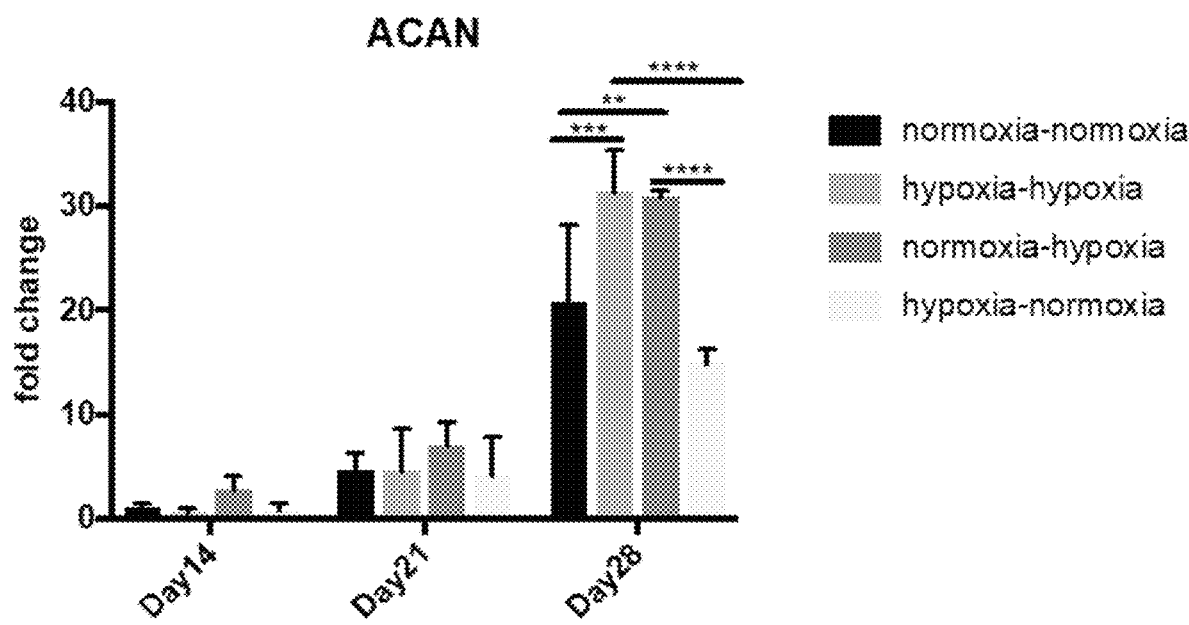
Figure 10C:
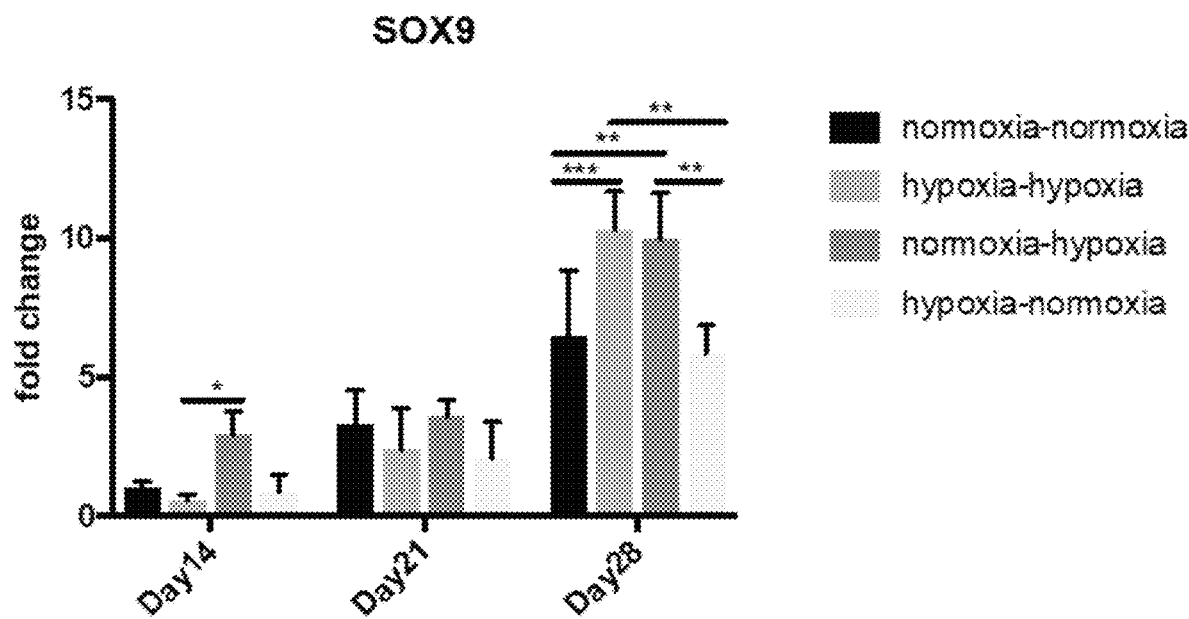
Figure 10D:
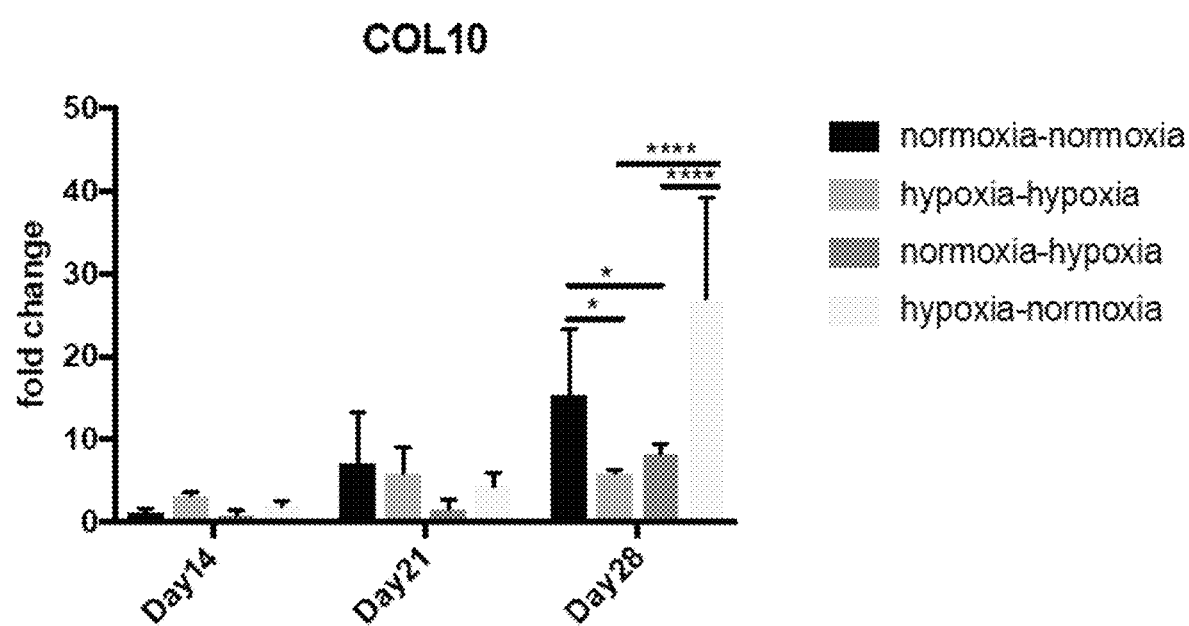
Figure 10E:
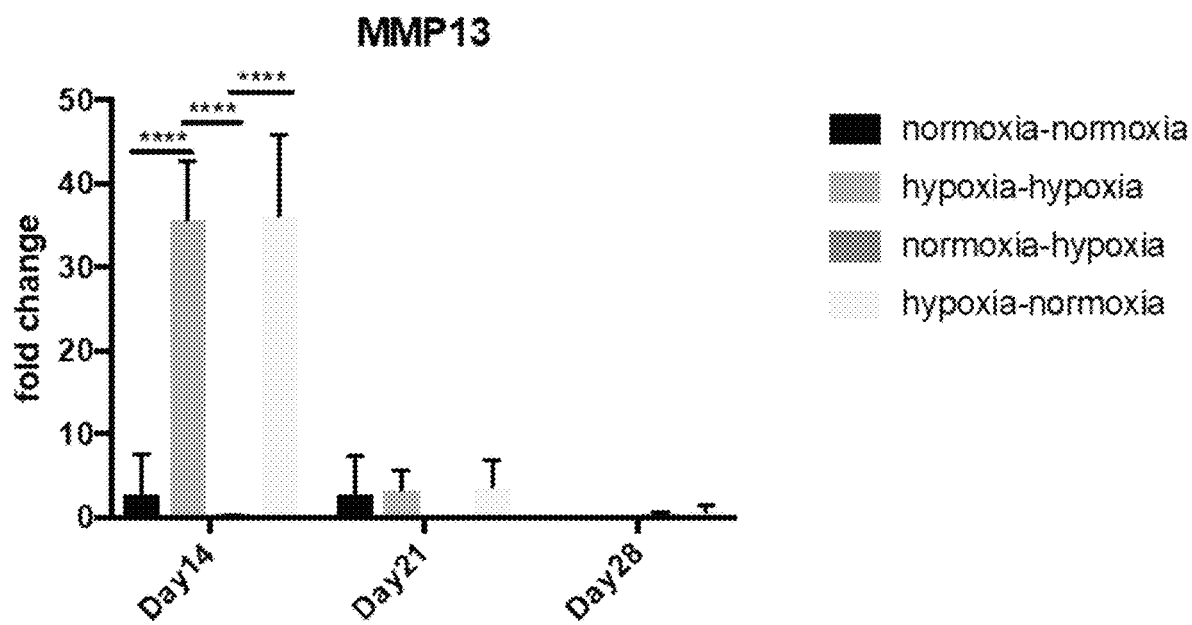

In the push-out mechanical testing, pellet group displayed a higher peak force (FIG. 8D). However large fissure was seen between cartilage and implant in histology in pellet group, suggesting poor integration between implant and host tissues. Such gap was not observed in MSC-mECM group (FIG. 7). Based on the histology, we further assessed the integration between the graft and the explant by measuring the length of area that has no gap. Results showed that MSC-mECM group had a 97% integration, which was only 20% in pellet group. The reason for the seemingly contradictory result may lied in the fact that MSC-pellet group showed strong calcification at the junction between grafts and host cartilage tissue, while MSC-mECM group had much less, or negative, positive staining. In vivo implantation further showed that MSC-mECM formed a compact, uniform and cartilage-like construct (FIG. 9).

Example 2

Effect of Oxygen Tension on the Property of Cartilage

The methods to generate MSC-mECM and induce chondrogenic differentiation have been described above.

During the process of depositing ECM, MSCs were cultured under normoxic (20% O$_2$ atmosphere) or hypoxic (2% O$_2$ atmosphere) conditions for 10 days, to make MSC-mECM. Afterwards, the MSC-mECM were treated with trypsin and subjected to chondrogenic culture for another 28 days, under normoxic or hypoxic conditions. (See FIG. 3, with the vertical line separating the two phases). Finally, we have 4 groups, with different oxygen tensions in condensation and chondrogenesis stages (normoxia-normoxia; hypoxia-hypoxia; normoxia-hypoxia; hypoxia-normoxia). Real time PCR and safranin O staining are used to assess the cartilage formation.

Figure 11:
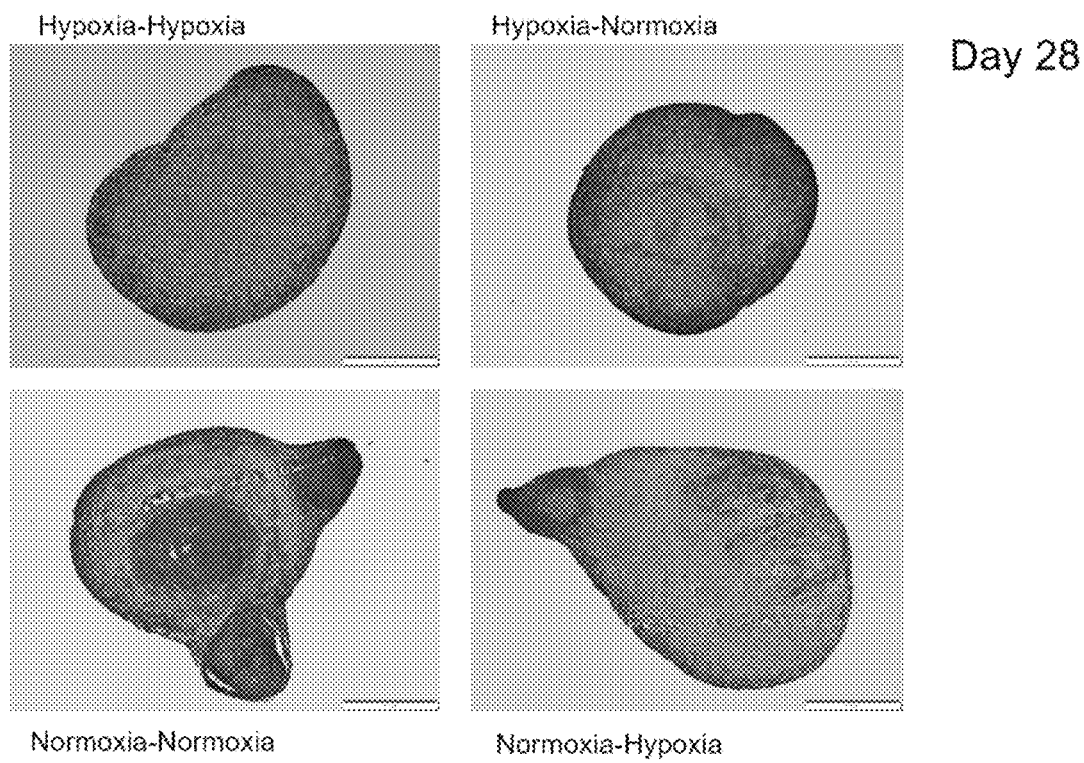
FIG. 11 provides photographs of Safranin O/Fast Green-stained cartilage material prepared according to Example 2, at day 28 of culture in chondrogenic medium. Lighters area indicate more deposition of sGAG.

Gene expression levels of collagen type IIA1(COL2A1) (FIG. 10A), aggrecan (ACAN, FIG. 10B), SRY-Box 9 transcription factor (SOX9, FIG. 10C), collagen type X (COL10, FIG. 10D), and matrix metalloproteinase 13 (MMP13, FIG. 10E) were analyzed by RT-PCR, as described above. FIGS. 10A-10E indicate that with hypoxic conditions applied during chondrogenesis exhibiting superior results. It is noted that all samples prepared as described in Example 1 eventually produced cartilaginous material over time (see, FIG. 11), the samples cultured under hypoxic conditions during chondrogenesis (e.g., after trypisinization and in chondrogenic medium) resulted in superior gene expression patterns, with lower hypertrophic gene expression profiles, and more rapid and better production of the cartilaginous material in the first 28 days (FIG. 11).

The following numbered clauses describe various exemplary aspects and embodiments of the present invention.

Clause 1. A method of preparing cartilaginous material, comprising:
  culturing mesenchymal stem cells in vitro on a cell culture substrate past confluence to produce a tissue structure comprising mesenchymal stem cells (MSCs) and mesenchymal stem cell-derived extracellular matrix (mECM);
  contacting the MSCs in the mECM (MSC-mECM) with a cell dissociating agent in an amount and for a duration sufficient to cause rounding of the MSCs in the MSC-mECM;
  removing the dissociating agent from the MSC-mECM; and
  culturing the dissociating agent-treated MSC-mECM in chondrogenic media, to produce cartilaginous material.

Clause 2. The method of clause 1, wherein the mesenchymal stem cells are bone marrow-derived mesenchymal stem cells, adipose-derived mesenchymal stem cells, umbilical cord blood-derived mesenchymal stem cells, umbilical cord matrix-derived mesenchymal stem cells, hamstring tendon-derived mesenchymal stem cells, bone-derived mesenchymal stem cells, muscle-derived mesenchymal stem cells, synovium-derived mesenchymal stem cells, and other adult tissue-derived mesenchymal stem cells, or induced pluripotent stem cells.

Clause 3. The method of clause 2, wherein the mesenchymal stem cells are adipose-derived mesenchymal stem cells.

Clause 4. The method of clause 2, wherein the mesenchymal stem cells are bone marrow-derived mesenchymal stem cells.

Clause 5. The method of any one of clauses 1-4, wherein the chondrogenic medium comprises a chondrogenic growth factor.

Clause 6. The method of clause 5, wherein the chondrogenic growth factor is transforming growth factor beta-1 (TGF-β1), transforming growth factor beta-3 (TGF-β3), bone morphogenetic protein 2 (BMP2), bone morphogenetic protein 6 (BMP6), growth differentiation factor 5 (GDF5), or fibroblast growth factor 18 (FGF18), or a combination of any two or more of the preceding.

Clause 7. The method of any one of clauses 1-6, wherein the dissociating agent is a protease.

Clause 8. The method of clause 7, wherein the protease is trypsin.

Clause 9. The method of any one of clauses 1-6, wherein the dissociating agent is trypsin-EDTA.

Clause 10. The method of any one of clauses 1-6, wherein the dissociating agent is a chelating agent.

Clause 11. The method of clause 10 wherein the chelating agent is EDTA or EGTA, or a combination thereof.

Clause 12. The method of any one of clauses 1-11, wherein when the MSC-mECM is contacted with the dissociating agent in an amount and for a duration sufficient to cause rounding of cells in the mECM, the MSCs are not substantially separated (e.g., released, dissociated, or detached) from the mECM.

Clause 13. The method of any one of clauses 1-12, wherein the MSC-mECM is cultured under hypoxic conditions during chondrogenesis.

Clause 14. The method of any one of clauses 1-13, wherein the mesenchymal stem cells are cultured under hypoxic conditions during formation of the mECM.

Clause 15. The method of clause 13 or 14, wherein, for hypoxic conditions, the amount of oxygen in the culture medium is lower than in culture medium maintained in a normoxic atmosphere of 20% to 23% oxygen, or the partial pressure of oxygen in the culture medium relative to all dissolved gasses in the culture medium, is less than 20%, 10% or lower, from 1% to 5%, for example, from 1% to 3%, or 2%, of the total dissolved gas content in the culture medium.

Clause 16. The method of any one of clauses 1-12, wherein the mesenchymal stem cells are cultured in a normoxic atmosphere (20% to 23% $O_2$) prior to contacting the mECM with the dissociating agent.

Clause 17. The method of any one of clauses 1-15, wherein the mECM is released from the cell culture substrate after contacting the mECM with the dissociating agent and prior to culture in the chondrogenic medium.

Clause 18. The method of any one of clauses 1-17, wherein the mesenchymal stem cells are cultured on the cell culture substrate ex vivo past confluence in culture medium comprising ascorbic acid (e.g., L-ascorbic acid or vitamin C).

Clause 19. A method of producing a cartilage material in a patient, comprising implanting a cartilaginous material prepared according to any one of clauses 1-18 in an anatomical site in a patient.

Clause 20. The method of clause 19, wherein the anatomical site is a location of cartilage injury, damage, insufficiency, deficiency or defect in the patient, e.g., articular or hyaline cartilage injury, damage, insufficiency, deficiency or defect in the patient.

Clause 21. The method of clause 19 or 20, wherein the mesenchymal stem cells are autologous or allogeneic to the patient.

Having described this invention, it will be understood to those of ordinary skill in the art that the same can be performed within a wide and equivalent range of conditions, formulations and other parameters without affecting the scope of the invention or any embodiment thereof.

What we claim is:

1. A method of preparing cartilaginous material, comprising:
  culturing mesenchymal stem cells in vitro on a cell culture substrate past confluence to produce a tissue structure comprising mesenchymal stem cells (MSCs) and mesenchymal stem cell-derived extracellular matrix (mECM);
  contacting the MSCs in the mECM (MSC-mECM) with a cell dissociating agent in an amount and for a duration sufficient to cause rounding of the MSCs in the MSC-mECM, such that the rounded cells remain at least partially attached to the mECM;

removing the dissociating agent from the MSC-mECM; and culturing the dissociating agent-treated MSC-mECM in chondrogenic media to produce pellets, comprising round MSCs and mECM, thereby producing cartilaginous material.

2. The method of claim 1, wherein the mesenchymal stem cells are bone marrow-derived mesenchymal stem cells, adipose-derived mesenchymal stem cells, umbilical cord blood-derived mesenchymal stem cells, umbilical cord matrix-derived mesenchymal stem cells, hamstring tendon-derived mesenchymal stem cells, bone-derived mesenchymal stem cells, muscle-derived mesenchymal stem cells, synovium-derived mesenchymal stem cells, other adult tissue-derived mesenchymal stem cells, or induced pluripotent stem cells (iPSCs) and multipotent cells derived from iPSCs.

3. The method of claim 2, wherein the mesenchymal stem cells are adipose-derived mesenchymal stem cells.

4. The method of claim 2, wherein the mesenchymal stem cells are bone marrow-derived mesenchymal stem cells.

5. The method of claim 1, wherein the chondrogenic medium comprises a chondrogenic growth factor.

6. The method of claim 5, wherein the chondrogenic growth factor is transforming growth factor beta-1 (TGF-β1), transforming growth factor beta-3 (TGF-β-3), bone morphogenetic protein 2 (BMP2), bone morphogenetic protein 6 (BMP6), growth differentiation factor 5 (GDF5), or fibroblast growth factor 18 (FGF18), or a combination of any two or more of the preceding.

7. The method of claim 1, wherein the dissociating agent is a protease.

8. The method of claim 7, wherein the protease is trypsin.

9. The method of claim 1, wherein the dissociating agent is trypsin-EDTA.

10. The method of claim 1, wherein the dissociating agent is a chelating agent.

11. The method of claim 10, wherein the chelating agent is EDTA or EGTA, or a combination thereof.

12. The method of claim 1, wherein the MSC-mECM is cultured under hypoxic conditions during chondrogenesis.

13. The method of claim 12, wherein the mesenchymal stem cells are cultured under normoxic conditions during formation of the mECM.

14. The method of claim 1, wherein the mesenchymal stem cells are cultured under hypoxic conditions during formation of the mECM.

15. The method of claim 1, wherein the mECM is released from the cell culture substrate after contacting the mECM with the dissociating agent and prior to culture in the chondrogenic medium.

16. The method of claim 1, wherein the mesenchymal stem cells are cultured on the cell culture substrate ex vivo past confluence in culture medium comprising ascorbic acid.

17. The method of claim 1, wherein the cartilaginous material is hyaline cartilage.

18. A method of producing a cartilage material in a patient, comprising implanting a cartilaginous material prepared according to claim 1 in an anatomical site in a patient.

19. The method of claim 18, wherein the anatomical site is a location of cartilage injury, damage, insufficiency, deficiency or defect in the patient.

20. The method of claim 18, wherein the cartilaginous material prepared according to claim 1 is prepared from mesenchymal stem cells that are autologous or allogeneic to the patient.

* * * * *